US005686389A

United States Patent [19]

Feistner

[11] Patent Number: 5,686,389

[45] Date of Patent: Nov. 11, 1997

[54] GROWTH INHIBITION OF ERWINIA AMYLOVORA

[75] Inventor: Gottfried J. Feistner, Rancho Cucamonga, Calif.

[73] Assignee: City of Hope, Duarte, Calif.

[21] Appl. No.: 564,093

[22] PCT Filed: Apr. 13, 1994

[86] PCT No.: PCT/US94/04002

§ 371 Date: Apr. 9, 1996

§ 102(e) Date: Apr. 9, 1996

[87] PCT Pub. No.: WO95/28378

PCT Pub. Date: Oct. 26, 1995

[51] Int. Cl.$^6$ .............................. A01N 25/02; A01N 31/02

[52] U.S. Cl. .............................. 504/147; 504/148

[58] Field of Search .............................. 504/147, 148

[56] References Cited

PUBLICATIONS

Tschierske et al., Dechema Biotechnology Conf. (1992), 5 (Pt. B), 761–4.

Primary Examiner—Phyllis G. Spivack
Attorney, Agent, or Firm—Rothwell, Figg, Ernst & Kurz

[57] ABSTRACT

Fire blight control agents that comprise salts of 5-hydroxylysine or 1,4-diamino-2-butanone in an aqueous solution are disclosed to inhibit the growth of *E. Amylovora*, the etiological agent of fire blight.

10 Claims, No Drawings

GROWTH INHIBITION OF *ERWINIA AMYLOVORA*

FIELD OF THE INVENTION

This invention relates to the control of fire blight disease by inhibition of the growth of *Erwinia amylovora* (*E. amylovora*). More particularly, the invention relates to novel fire blight control agents which comprise 5-hydroxylysine or 1,4-diamino-2-butanone in concentrations effective to inhibit the growth of *E. amylovora*.

BACKGROUND

Fire blight is one of the longest known and most feared plant diseases (1). Originally only found in North America, it is now also established in Central and South America, Europe, the Middle East, and New Zealand and is expected to arrive on the Australian Continent in the near future (2,3). Fire blight affects many members of the Rosaceae, including all species of the Pomoideae, and is especially destructive to pear and apple (1). Since the 1970's, *E. amylovora* has been controlled in the U.S. mainly by the antibiotic streptomycin. However, this practice is known to select for antibiotic-resistant strains. Since resistance genes are freely shared between bacterial species, and streptomycin is also used for the treatment of bacterial infections such as tuberculosis in humans, this practice is cause for concern. In fact, many European countries do not allow the use of antibiotics in agriculture, and typically destroy their fire blighted trees. Streptomycin-resistance in *E. amylovora* is indeed spreading, especially in the western United States. The Eastern United States are not affected yet, possibly because of a different spraying regimen (4). In addition to human health concerns, the spread of streptomycin-resistant strains of *E. amylovora* presents a serious economic threat to apple and pear growers in the United States because of the lack of alternative control agents for fire blight. Terramycin-streptomycin combinations have been shown to delay streptomycin-resistance in laboratory trials (4). Biological control of fire blight with suitable epiphytic bacteria (5), for example *Erwinia herbicola* or Pseudomonas species (6,7), or with plant extracts (8) provides protection to some degree but not with the same efficacy as streptomycin. The search for alternative synthetic control agents therefore continues, especially in Europe and Japan (9). However, most of the current efforts to achieve control of fire blight follow a trial and error approach.

SUMMARY OF THE INVENTION

This invention provides novel, antibiotic free, apparently environmentally friendly, fire blight control agents. It is based on the discovery that 5-hydroxylysine and 1,4-diamino-2-butanone inhibit the growth of *E. amylovora*. Accordingly, one embodiment of the invention comprises formulations for application to Rosaceae plants infected or at risk of infection with fire blight which contain 5-hydroxylysine or 1,4-diamino-2-butanone in an amount effective to inhibit the growth of *E. amylovora*. The invention also includes fire blight control agents which comprise combinations of 5-hydroxylysine with 1,4-diamino-2-butanone and a combination of either or both of such compounds with streptomycin or other agents which inhibit the growth of *E. amylovora*. Another embodiment of the invention comprises epiphytic microorganisms which express 5-hydroxylysine or 1,4-diamino-2-butanone and the delivery of such microorganisms by spraying or by insects to the blossoms of Rosaceae plants to inhibit the growth of *E. amylovora*.

DETAILED DESCRIPTION OF THE INVENTION

Plant pathologists use forecasting systems based on time of year, humidity, temperature and related parameters to predict fire blight risk (10). Evidence indicative of high fire blight danger conventionally triggers the initiation of spraying, usually with streptomycin. A novel fire blight control agent is urgently needed, however, because *E. amylovora* is becoming resistant to streptomycin and because the use of antibiotics in agriculture is precluded in several affected countries.

The novel, non-antibiotic, fire blight control agents provided by this invention contain 5-hydroxylysine or 1,4-diamino-2-butanone or a combination thereof in amounts effective to inhibit the growth of *E. amylovora* on fire blight vulnerable or infected plants. The discovery that 5-hydroxylysine inhibits the growth of *E. amylovora* was quite unexpected because it is a normal component of human collagen and the lysine decarboxylase of the related enterobacterium, *Escherichia coli*, is known to use 5-hydroxylysine as a substrate. 1,4-diamino-2-butanone has previously been reported to be fungicidal, for example, to inhibit powdery mildew on apple with an $EC_{50}=72$ ppm (11), but is not yet known as a growth inhibitor for *E. amylovora*.

5-Hydroxylysine Fire Blight Control Agents 5-hydroxylysine contains two asymmetric carbon atoms, namely, C-2 and C-5. Their configuration may be either S or R (or L and D acceding to an older convention) and thus a number of stereoisomers exist. This invention includes fire blight control agents which contain any or all of these stereoisomeric forms of 5-hydroxylysine. Accordingly, as used in this specification and the claims, the term 5-hydroxylysine means either of the (2S, 5S), (2R, 5R), (2S, 5R) or (2R, 5S) isomers or any mixture thereof, including but not limited to racemic mixtures.

This invention includes all 5-hydroxylysine formulations that are useful for application to plants in any desired manner to inhibit or control fire blight.

In one embodiment of the invention, 5-hydroxylysine is applied as a solution in an appropriate solvent, preferably water, or aqueous solvents with suitable performance-enhancing additives. The 5-hydroxylysine may be neutralized and thus will be protonated in the solvent solution.

A preferred fire blight control agent comprises an aqueous solution having a pH of 5 to 8 of 5-hydroxylysine hydrochloride. Other water soluble 5-hydroxylysine salts such as sulfates, phosphates, or acetates are also embraced by this invention.

Pursuant to this invention, these novel fire blight control agents contain at least about 0.02 ppm, the apparent threshold *E. amylovora* inhibition level, and preferably about 0.2 to 200 ppm of 5-hydroxylysine. As Example II shows, solutions containing 2000 ppm of 5-hydroxylysine inhibit the growth of *E. amylovora*. There is no apparent critical upper concentration limit. Thus, one embodiment of the invention includes concentration ranges of 0.2 to 2000 ppm of 5-hydroxylysine.

Another embodiment of this invention comprises the dispersal of powdery 5-hydroxylysine preparations by honey bees. The bees would be forced to walk through such 5-hydroxylysine preparations as they exit from their hives.

1,4-Diamino-2-Butanone Fire Blight Control Agents

The fire blight control agents of this invention also comprise powdery preparations of 1,4-diamino-2-butanone or aqueous solutions having a pH of 5 to 8.

Aqueous solutions containing at least 25 ppm, the apparent threshold E. amylovora inhibition level, and preferably 25 to 200 ppm of protonated 1,4-diamino-2-butanone dihydrochloride are suggested. There is no apparent critical upper concentration limit. As Example IV shows, an aqueous solution containing 2000 ppm of 1,4-diamino-2-butanone dihydrochloride inhibits the growth of E. amylovora. Thus, one embodiment of this invention includes aqueous solutions containing 25 to 2000 ppm of 1,4-diamino-2-butanone.

The fire blight control agents of this invention include mixtures of 5-hydroxylysine and 1,4-diamino-2-butanone in any proportion, either as a powdery preparation or in aqueous solution having a pH of 5 to 8. The concentration of 5-hydroxylysine and 1,4-diamino-2-butanone in such mixtures should equal or exceed the respective threshold levels of inhibition of E. amylovora growth. One embodiment of the invention comprises an aqueous solution having a pH of 5 to 8 containing 0.2 to 200 ppm of 5-hydroxylysine and from 25 to 200 ppm of 1,4-diamino-2-butanone.

The aqueous solutions which comprise the preferred fire blight control agents of this invention may also contain spray adjuvants to facilitate absorption of the growth retardant by plant tissue.

The novel fire blight control agents are applied in known manner, e.g., by spraying to plants in need thereof or via the disperal by honey bees. The invention also includes sequential application, e.g., by spraying solutions of 5-hydroxylysine and 1,4-diamino-2-butanone or of either or both of 5-hydroxylysine or 1,4-diamino-2-butanone and streptomycin and other fire blight control agents.

EXAMPLE I

This Example describes the formulation of the minimal growth medium and the cultivation procedures used in each of the ensuing Examples II through V. The minimal medium growth medium consisted of an aqueous solution of 2 grams per liter of $K_2HPO_4.3\ H_2O$; 0.1 grams per liter of $MgSO_4.7\ H_2O$; 0.4 grams per liter of $(NH_4)_2SO_4$; 2 grams per liter of sucrose, 100 μg per liter of nicotinic acid and ferric citrate in a concentration of $1\times10^{-8}$ molar. The pH was adjusted to 7 by sulfuric acid. In each example cultivation was in 50 ml batches in 250 ml flasks at room temperature (18°–25° C.) under moderate stirring (Bellco nine position magnetic stirrer, speed 4–5; Bellco Glass, Inc., Vineland, N.J.).

EXAMPLE II

A sterile, aqueous solution of 5-hydroxylysine hydrochloride (mixed DL and DL allo; Sigma) having a pH of 7 was added in an amount to provide 2000 ppm of 5-hydroxylysine to a 50 ml batch of growth medium (as described in Example I) which had been inoculated with E. amylovora scraped from an Agar plate. No growth of E. amylovora was observed for nine days.

EXAMPLE III

A batch of growth medium as described in Example I was inoculated with a single drop of an existing E. amylovora culture and thereafter divided into ten 50 ml aliquots. Sterile, aqueous solutions of 5-hydroxylysine hydrochloride as described in Example II were added in the amounts indicated in Table 1. Cultivation ensued as described in Example I. Growth was observed visually and by periodic optical density measurements at 620 nm on a 1 ml sample withdrawn from the cultures, using a Beckman DU-7 spectrophotometer and standard 10 mm cuvettes. Dilution series results reported in Table 1 establish an inhibition threshold level for 5-hydroxylysine of approximately 0.02 ppm.

TABLE 1

Inhibition of Erwinia amylovora by 5-Hydroxylysine

| [Hyl] (ppm) | Day 2 | Day 3 | Day 4 | Day 5 | Day 6 | Day 7 | Day 8 |
|---|---|---|---|---|---|---|---|
| 20.0 | — | — | — | — | 0.00 | — | — |
| 20.0 | — | — | — | — | 0.00 | — | — |
| 2.0 | — | — | — | 0.04 | 1.04 | | |
| 2.0 | — | — | — | 0.03 | 1.03 | | |
| .2 | — | — | 0.00 | 0.13 | 0.99 | | |
| .2 | — | — | 0.00 | 0.07 | 1.03 | | |
| .02 | — | 0.03 | 0.46 | 1.04 | | | |
| .02 | — | 0.01 | 0.57 | 1.02 | | | |
| None | — | 0.97 | | | | | |
| None | — | 0.88 | | | | | |

EXAMPLE IV

Example II was repeated with the exception that 2000 ppm of 1,4-diamino-2-butanone dihydrochloride (Aldrich), pH 7, was added to the inoculated growth medium instead of 5-hydroxylysine hydrochloride. No growth was observed for eight days. The culture supernatant turned black, presumably due to oxidation.

EXAMPLE V

Example III was repeated with the exception that sterile, aqueous solutions of 1,4-diamino-2-butanone dihydrochloride (Aldrich), pH 7 were added in the amounts indicated in Table 2. Dilution series results reported in Table 2 indicate an inhibition threshold level of approximately 25 ppm.

TABLE 2

Inhibition of Erwinia amylovora by 1,4-diamino-2-butanone

| [Inhibitor] (ppm) | Day 2 | Day 3 | Day 4 | Day 5 | Day 6 | Day 7 |
|---|---|---|---|---|---|---|
| 25.0 | — | 0.41 | | | | |
| 25.0 | — | 0.75 | | | | |
| 2.5 | — | 1.09 | | | | |
| 2.5 | — | 1.08 | | | | |
| .25 | — | 1.09 | | | | |
| .25 | — | 1.07 | | | | |
| .025 | — | 1.11 | | | | |
| .025 | — | 1.08 | | | | |
| None | — | 1.06 | | | | |
| None | — | 0.52 | | | | |

BIBLIOGRAPHY 1. van der Zwet, T., et al. *Fire blight. A bacterial disease of rosaceous plants*, Washington, D.C., United States Department of Agriculture (1979).
2. Fahy, P. C., et al., *Plant Prot. Q.* 6:34–38 (1991).
3. Sellwood, J. E., British Crop Protection Monograph No. 54. Plant Health and the European Single Market; Meeting, Reading, England, U.K., Mar. 30–Apr. 1, 1993, pp. 313–316.
4. Burr, T. J., et al., *Plant Disease* 77:63–66 (1993).
5. Naumann, K., et al., *Wissenschaftliche Tagung Über den Feuerbrand*, Ladenburg, FRG, Kommissionsverlag Paul Parey, Berlin, p. 54–58 (1992).

6. Johnson, K. B., et al., *Phytopathology* 83:995–1002 (1993).

7. Thomson, S. V., et al., *Plant Disease* 76:1052–1056 (1992).

8. Mosch, J., et al., *Wissenschaftliche Tagung Über den Feuerbrand*, Ladenburg, FRG, Kommissionsverlag Paul Parey, Berlin, p. 48–53 (1992).

9. Zeller, W., *Wissenschaftliche Tagung Über den Feuerbrand*, Ladenburg, FRG, Kommissionsverlag Paul Parey, Berlin, p. 44–47 (1992).

10. Van der Zwet, T., et al., U.S. Department of Agriculture, Agriculture Information Bulletin No. 631 (1991).

11. Foster, et al., *Pestic. Sci.* 37:267–272 (1993).

I claim:

1. A method for inhibiting fire blight disease in a plant which comprises providing an aqueous medium having a pH of 5 to 8 containing 5-hydroxylysine or a hydrochloride salt thereof in an amount effective to inhibit the growth of *E. amylovora* and applying said medium to a plant having fire blight.

2. The method of claim 1 wherein said aqueous solution contains 5-hydroxylysine dihydrochloride.

3. A method as defined by claim 1 in which said aqueous medium contains from 0.2 to 200 ppm of 5-hydroxylysine.

4. A method as defined by claim 1 in which said aqueous medium contains at least 0.02 ppm of 5-hydroxylysine.

5. A method for inhibiting the growth of *E. Amylovora* on a plant at risk of fire blight infection which comprises (i) determining whether a plant is at risk of fire blight infection;

(ii) applying to said plant, if determined to be at risk of fire blight infection, a fire blight control agent comprising an aqueous solution having a pH of 5 to 8 containing at least 0.02 ppm of a hydrochloride salt 5-hydrolysine or at least 25 ppm of a hydrochloride salt 1,4-diamino-2-butanone at a time and in an amount effective to inhibit the growth of *E. amylovora* on said plant.

6. A method as defined by claim 5 in which said aqueous solution contains from 0.02 to 2000 ppm of 5-hydroxylysine hydrochloride.

7. A method as defined by claim 5 in which said aqueous solution contains from 25 to 2000 ppm of 1,4-diamino-2-butanone dihydrochloride.

8. An inhibitory growth medium for *E. amylovora* which comprises an aqueous solution containing at least 0.02 ppm of 5-hydroxylysine or at least 25 ppm of 1,4-diamino-2-butanone.

9. A fire blight control agent comprising an aqueous solution of 5-hydroxylysine hydrochloride, said solution having a pH of 5 to 8 and containing from 0.2 to 200 ppm of said 5-hydroxylysine hydrochloride in an amount effective to inhibit the growth of *E. Amylovora* and further comprising streptomycin.

10. A fire blight control agent as defined by claim 9 in which said aqueous solution also contains from 25 to 200 ppm of 1,4-diamino-2-butanone dihydrochloride.

* * * * *